United States Patent
Sato et al.

(10) Patent No.: US 11,083,430 B2
(45) Date of Patent: Aug. 10, 2021

(54) RADIATION IMAGING APPARATUS, CONTROL METHOD OF THE SAME, CONTROL APPARATUS, AND RADIATION IMAGING SYSTEM

(71) Applicant: CANON KABUSHIKI KAISHA, Tokyo (JP)

(72) Inventors: Sho Sato, Tokyo (JP); Minoru Watanabe, Yokohama (JP); Keigo Yokoyama, Kawasaki (JP); Kentaro Fujiyoshi, Tokyo (JP); Jun Kawanabe, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 99 days.

(21) Appl. No.: 16/672,824

(22) Filed: Nov. 4, 2019

(65) Prior Publication Data
US 2020/0060639 A1    Feb. 27, 2020

Related U.S. Application Data

(63) Continuation of application No. PCT/JP2018/009857, filed on Mar. 14, 2018.

(30) Foreign Application Priority Data

May 9, 2017    (JP) .............................. JP2017-093374

(51) Int. Cl.
*H05G 1/42*    (2006.01)
*G01N 23/04*    (2018.01)
*A61B 6/00*    (2006.01)

(52) U.S. Cl.
CPC ..................................... *A61B 6/54* (2013.01)

(58) Field of Classification Search
CPC . H05G 1/42; G01N 23/04; A61B 6/54; A61B 6/542; A61B 6/42; A61B 6/4208;
(Continued)

(56) References Cited

U.S. PATENT DOCUMENTS 7,381,965 B2    6/2008    Ishii et al.
7,541,617 B2    6/2009    Mochizuki et al.
(Continued)

FOREIGN PATENT DOCUMENTS

JP    S61-294984    12/1986
JP    H09-285461    11/1997
(Continued)

OTHER PUBLICATIONS

U.S. Appl. No. 16/103,150, Atsushi Iwashita, filed Aug. 14, 2019.
(Continued)

*Primary Examiner* — Don K Wong
(74) *Attorney, Agent, or Firm* — Venable LLP

(57) ABSTRACT

The present invention provides a technique advantageous in suitably determining the irradiation end timing in a radiation imaging apparatus that can perform AEC.

The radiation imaging apparatus comprises a sensor configured to detect radiation and a control unit, wherein the control unit generates, after the start of radiation irradiation, an evaluation value indicating the stability of a radiation irradiation intensity based on a sensor signal from the sensor, and the control unit outputs, in response to the evaluation value satisfying a predetermined condition, a signal indicating that the radiation irradiation intensity has stabilized.

11 Claims, 10 Drawing Sheets

(58) Field of Classification Search
CPC ... A61B 6/4266; A61B 6/4275; A61B 6/4283; A61B 6/4241; A61B 6/425; A61B 6/548
See application file for complete search history.

(56) References Cited

U.S. PATENT DOCUMENTS

| | | | |
|---|---|---|---|
| 7,629,564 B2 | 12/2009 | Mochizuki et al. | |
| 7,645,976 B2 | 1/2010 | Watanabe et al. | |
| 7,750,422 B2 | 7/2010 | Watanabe et al. | |
| 7,812,313 B2 | 10/2010 | Mochizuki et al. | |
| 7,812,317 B2 | 10/2010 | Watanabe et al. | |
| 7,858,947 B2 | 12/2010 | Mochizuki et al. | |
| 7,923,695 B2 | 4/2011 | Ishii et al. | |
| 7,932,946 B2 | 4/2011 | Ishii et al. | |
| 8,067,743 B2 | 11/2011 | Ishii et al. | |
| 8,084,745 B2 | 12/2011 | Mochizuki et al. | |
| 8,154,641 B2 | 4/2012 | Nomura et al. | |
| 8,519,344 B2 | 8/2013 | Ishii et al. | |
| 8,680,472 B2 | 3/2014 | Mochizuki et al. | |
| 8,829,438 B2 | 9/2014 | Sato et al. | |
| 8,878,972 B2 | 11/2014 | Wayama et al. | |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,270,903 B2 | 2/2016 | Wayama et al. | |
| 9,277,896 B2 | 3/2016 | Ofuji et al. | |
| 9,423,512 B2 | 8/2016 | Sato et al. | |
| 9,423,513 B2 | 8/2016 | Watanabe et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,521,347 B2 | 12/2016 | Kawanabe et al. | |
| 9,541,653 B2 | 1/2017 | Iwashita et al. | |
| 9,625,585 B1 | 4/2017 | Yokoyama et al. | |
| 9,661,240 B2 | 5/2017 | Fujiyoshi et al. | |
| 9,675,307 B2 | 6/2017 | Ofuji et al. | |
| 9,726,767 B2 | 8/2017 | Kawanabe et al. | |
| 9,812,474 B2 | 11/2017 | Yagi et al. | |
| 9,835,732 B2 | 12/2017 | Fujiyoshi et al. | |
| 9,838,638 B2 | 12/2017 | Furumoto et al. | |
| 9,948,871 B2 | 4/2018 | Wayama et al. | |
| 9,977,135 B2 | 5/2018 | Yokoyama et al. | |
| 10,009,990 B2 | 6/2018 | Takenaka et al. | |
| 10,068,943 B2 | 9/2018 | Fujiyoshi et al. | |
| 10,197,684 B2 | 2/2019 | Terui et al. | |
| 10,206,642 B2 | 2/2019 | Hiroike | |
| 10,274,612 B2 | 4/2019 | Ishii et al. | |
| 10,473,801 B2 | 11/2019 | Kawanabe et al. | |
| 10,537,295 B2 | 1/2020 | Watanabe et al. | |
| 2011/0317054 A1 | 12/2011 | Kameshima et al. | |
| 2013/0148784 A1* | 6/2013 | Tajima | A61B 6/5294 378/62 |
| 2013/0342514 A1 | 12/2013 | Yokoyama et al. | |
| 2014/0151769 A1 | 6/2014 | Wayama et al. | |
| 2014/0154833 A1 | 6/2014 | Wayama et al. | |
| 2014/0239186 A1 | 8/2014 | Sato et al. | |
| 2014/0361189 A1 | 12/2014 | Kameshima et al. | |
| 2016/0270755 A1 | 9/2016 | Takenaka et al. | |
| 2018/0008215 A1 | 1/2018 | Wayama et al. | |
| 2018/0317868 A1 | 11/2018 | Terui et al. | |
| 2018/0328862 A1 | 11/2018 | Sato et al. | |
| 2019/0146103 A1 | 5/2019 | Ofuji et al. | |
| 2019/0391629 A1 | 12/2019 | Yokoyama et al. | |
| 2020/0008766 A1 | 1/2020 | Watanabe et al. | |
| 2020/0041664 A1 | 2/2020 | Furumoto et al. | |

FOREIGN PATENT DOCUMENTS

| | | |
|---|---|---|
| JP | 2013-138829 | 7/2013 |
| WO | 2014/208722 | 12/2014 |

OTHER PUBLICATIONS

U.S. Appl. No. 16/686,589, Kentaro Fujiyoshi, filed Nov. 18, 2019.
U.S. Appl. No. 16/720,989, Katsuro Takenaka, filed Dec. 29, 2019.

* cited by examiner

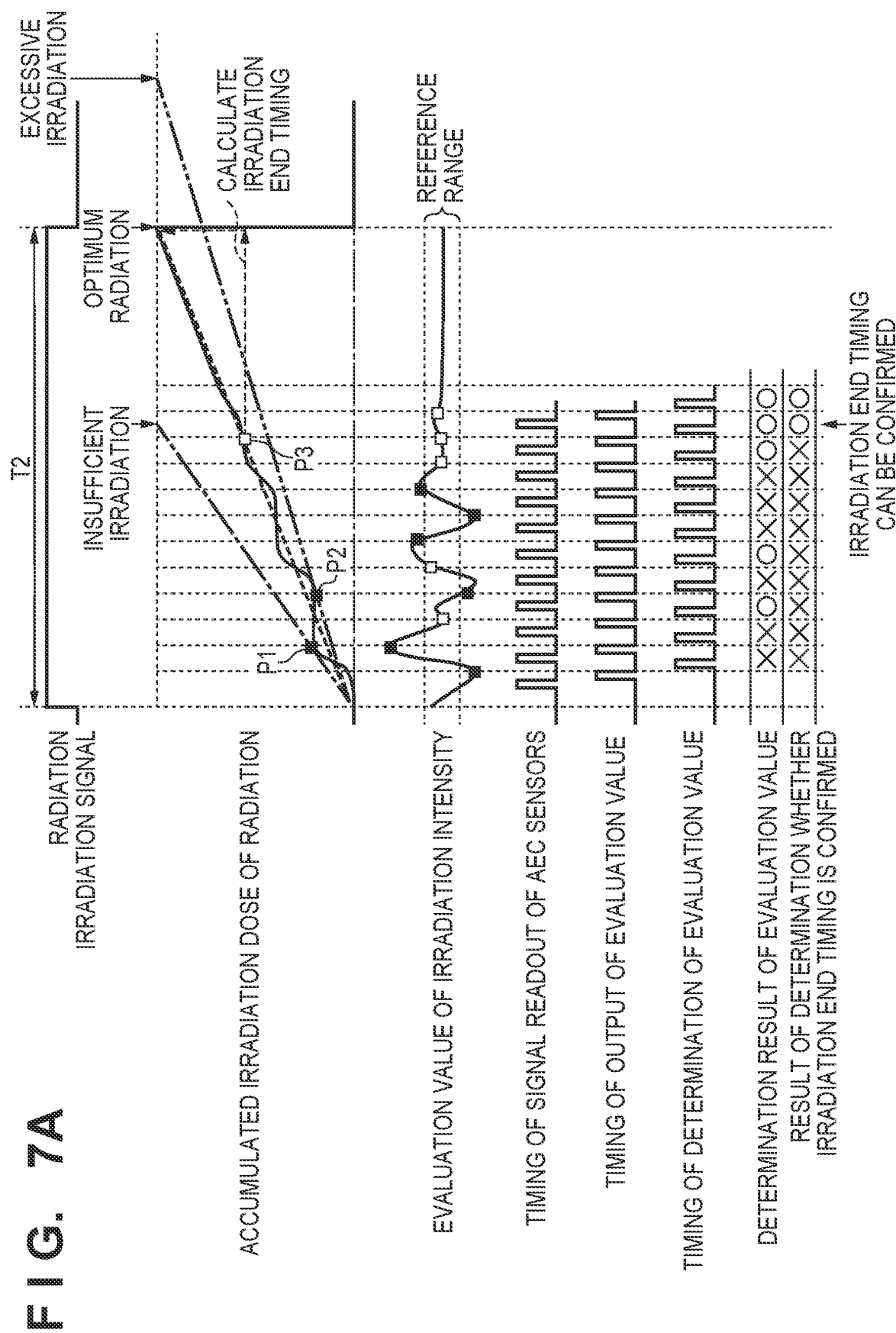

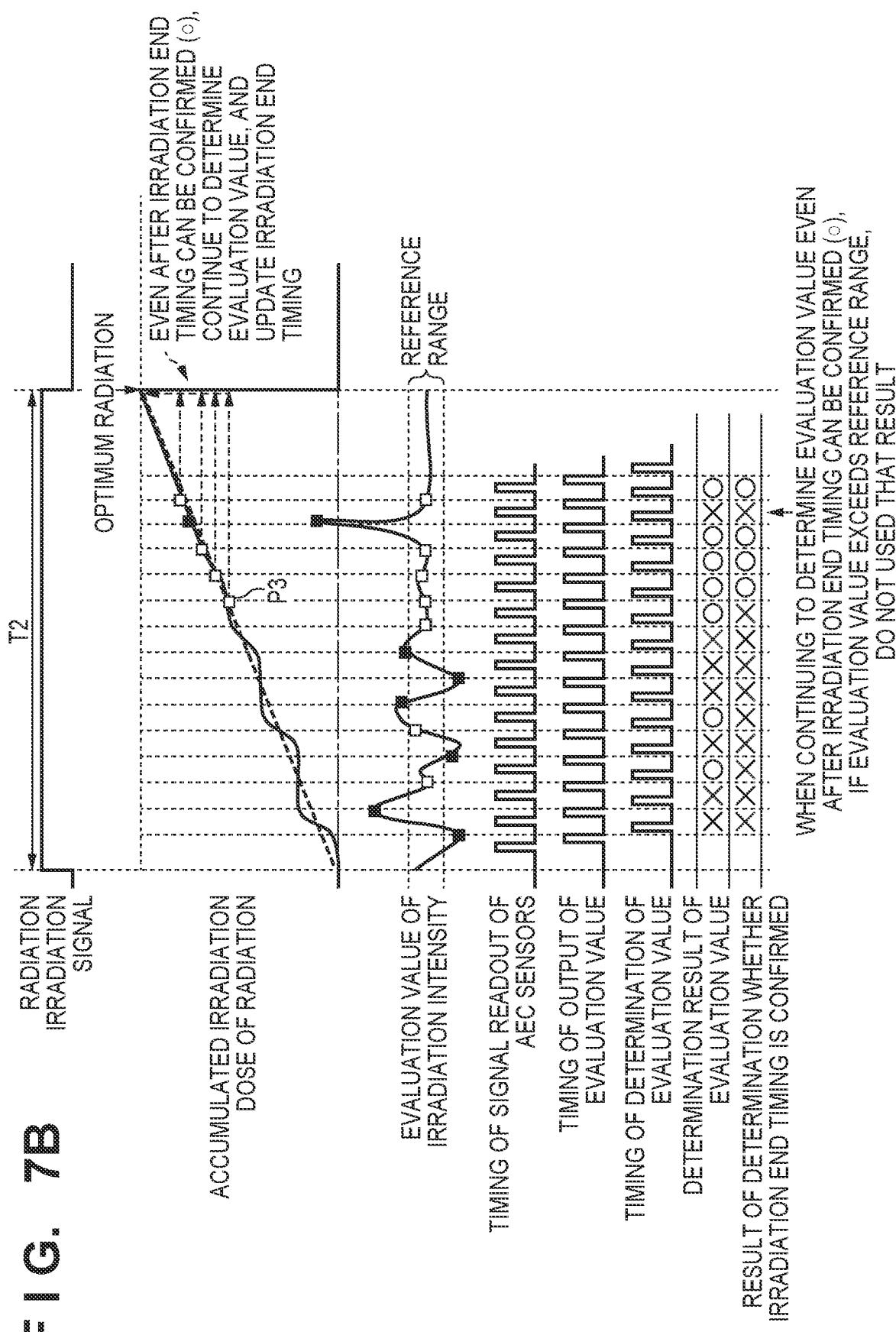

RADIATION IMAGING APPARATUS, CONTROL METHOD OF THE SAME, CONTROL APPARATUS, AND RADIATION IMAGING SYSTEM

CROSS-REFERENCE TO RELATED APPLICATIONS

This application is a Continuation of International Patent Application No. PCT/JP2018/009857, filed Mar. 14, 2018, which claims the benefit of Japanese Patent Application No. 2017-093374, filed May 9, 2017, both of which are hereby incorporated by reference herein in their entirety.

BACKGROUND OF THE INVENTION

Field of the Invention

The present invention relates to a radiation imaging apparatus, a control method of the same, a control apparatus, and a radiation imaging system.

Background Art

A radiation imaging apparatus performs imaging of internal tissues of a subject by detecting radiation emitted from a radiation source and passed through the subject. As one mode, the radiation irradiation time can be set based on an imaging condition (imaging target or the like).

Among radiation imaging apparatuses, there is an apparatus that is arranged to make an irradiation end request in response to the fact that a irradiation dose accumulated since the start of radiation irradiation has reached a reference value (PTL 1). That is, the radiation imaging apparatus can control the time in which radiation irradiation is performed by the radiation source described above. Such control is referred to as automatic exposure control (AEC) or the like.

CITATION LIST

Patent Literature

PTL 1: Japanese Patent Laid-Open No. 2013-138829

PTL 1 discloses that when a radiation irradiation end timing is to be determined (predicted) during radiation irradiation, the longer the time has elapsed from the start of radiation irradiation, the determination of the irradiation end timing can be performed with higher accuracy. However, the irradiation intensity of radiation from the radiation source may become unstable due to noise or the like in the radiation source or a detection value of this irradiation intensity in the radiation imaging apparatus may become unstable due to noise in the apparatus. Hence, it is difficult to uniquely confirm how much time should have elapsed for the determination of the irradiation end timing to be performed.

The object of the present invention is to provide a technique advantageous in suitably determining the irradiation end timing in a radiation imaging apparatus that can perform AEC.

SUMMARY OF THE INVENTION

An aspect of the present invention relates to a radiation imaging apparatus, and the radiation imaging apparatus is a radiation imaging apparatus that includes a sensor configured to detect radiation and a control unit, wherein the control unit generates, after the start of radiation irradiation, an evaluation value indicating the stability of a radiation irradiation intensity based on a sensor signal from the sensor, and the control unit outputs, in response to the evaluation value satisfying a predetermined condition, a signal indicating that the radiation irradiation intensity has stabilized.

Further features of the present invention will become apparent from the following description of exemplary embodiments with reference to the attached drawings.

BRIEF DESCRIPTION OF THE DRAWINGS

FIG. 7A is a timing chart for explaining a more specific example or a modification of the AEC;

FIG. 7B is a timing chart for explaining another more specific example or another modification of the AEC;

DESCRIPTION OF THE EMBODIMENTS

Figure 1:
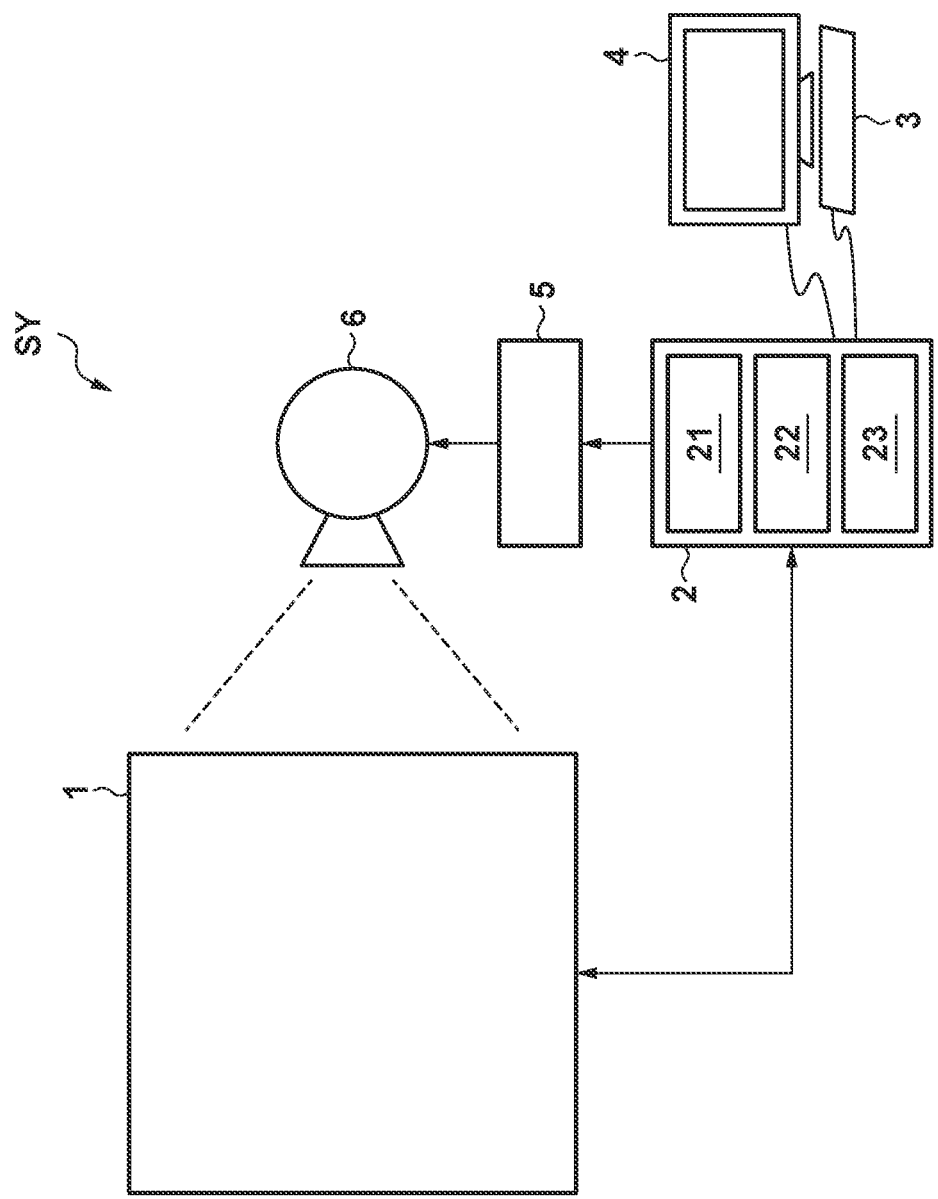
FIG. 1 is a block diagram for explaining an example of the arrangement of a radiation imaging system.

Preferred embodiments of the present invention will be described below with reference to the accompanying drawings. Note that each drawing is made for explaining the structure or arrangement, and the dimensions of the illustrated members do not necessarily reflect the actual dimensions. In addition, the same reference numerals denote the same members or constituent elements in these drawings, and a description of the overlapping contents will be omitted below.

First Embodiment

FIG. 1 is a system block diagram according to the first embodiment. The radiation imaging system SY includes a radiation imaging apparatus 1, a computer 2, an input terminal 3, a display 4, a radiation source control unit 5, and a radiation source 6. Although details will be described later, the radiation imaging apparatus 1 performs radiation imaging by detecting radiation emitted from the radiation source 6 and transmitted through a subject (patient or the like) (not shown). Although X-rays are used typically as the radiation, α-rays, β-rays, or the like may be used.

The computer 2 includes, for example, a CPU (central processing unit) 21, a memory 22, and an external interface 23, receives image data from the radiation imaging apparatus 1, processes the image data, and stores the image data or transmits the image data to another external unit. The computer 2 is connected to the input terminal 3 and the display 4, and a user (doctor or the like) can use the input terminal 3 to input, for example, pieces of imaging information such as information of the subject and the inspection target part, the condition of the radiation corresponding to the imaging information, and the like. The computer 2 causes the display 4 to display an image corresponding to the image data. Note that although it is assumed that a general-purpose personal computer will be used in this embodiment, a dedicated arithmetic operation apparatus or a control apparatus may be used as the computer 2.

The radiation source control unit 5 is connected to, for example, a switch (not shown) for starting a radiation irradiation operation, and drives the radiation source 6 in response to the switch being pressed by the user when the radiation imaging apparatus 1 is in an imaging enabled state. This causes the radiation source 6 to start radiation irradiation on the radiation imaging apparatus 1. As another embodiment, the radiation source control unit 5 may drive the radiation source 6 based on a signal indicating an imaging start request transmitted from the computer 2. In this case, the computer 2 can make an imaging start request based on an input made by the user on the input terminal 3 when the radiation imaging apparatus 1 is in the imaging enabled state. Note that, for example, a target value of the irradiation intensity or parameters of a tube current, tube voltage, and the like for implementing this target value are set to the radiation source control unit 5 via the input terminal 3, and the radiation source 6 is driven based on these settings.

The radiation irradiation time is determined based on the radiation irradiation intensity and an optimum value (a target value corresponding to the inspection target part) of the accumulated irradiation dose, and is determined by the radiation imaging apparatus 1. That is, after radiation irradiation is started, a radiation irradiation end request will be implemented automatically (that is, without requiring input by the user) by the radiation imaging apparatus 1. Such control is called automatic exposure control (AEC) in this specification.

The above-described arrangement is merely an example of the arrangement of the radiation imaging system SY, and the arrangement of the radiation imaging system SY is not limited to this. In addition, the connection between the components described above may be implemented by a wired connection such as a LAN cable or the like or a wireless connection such as Wi-Fi or the like.

Figure 2:
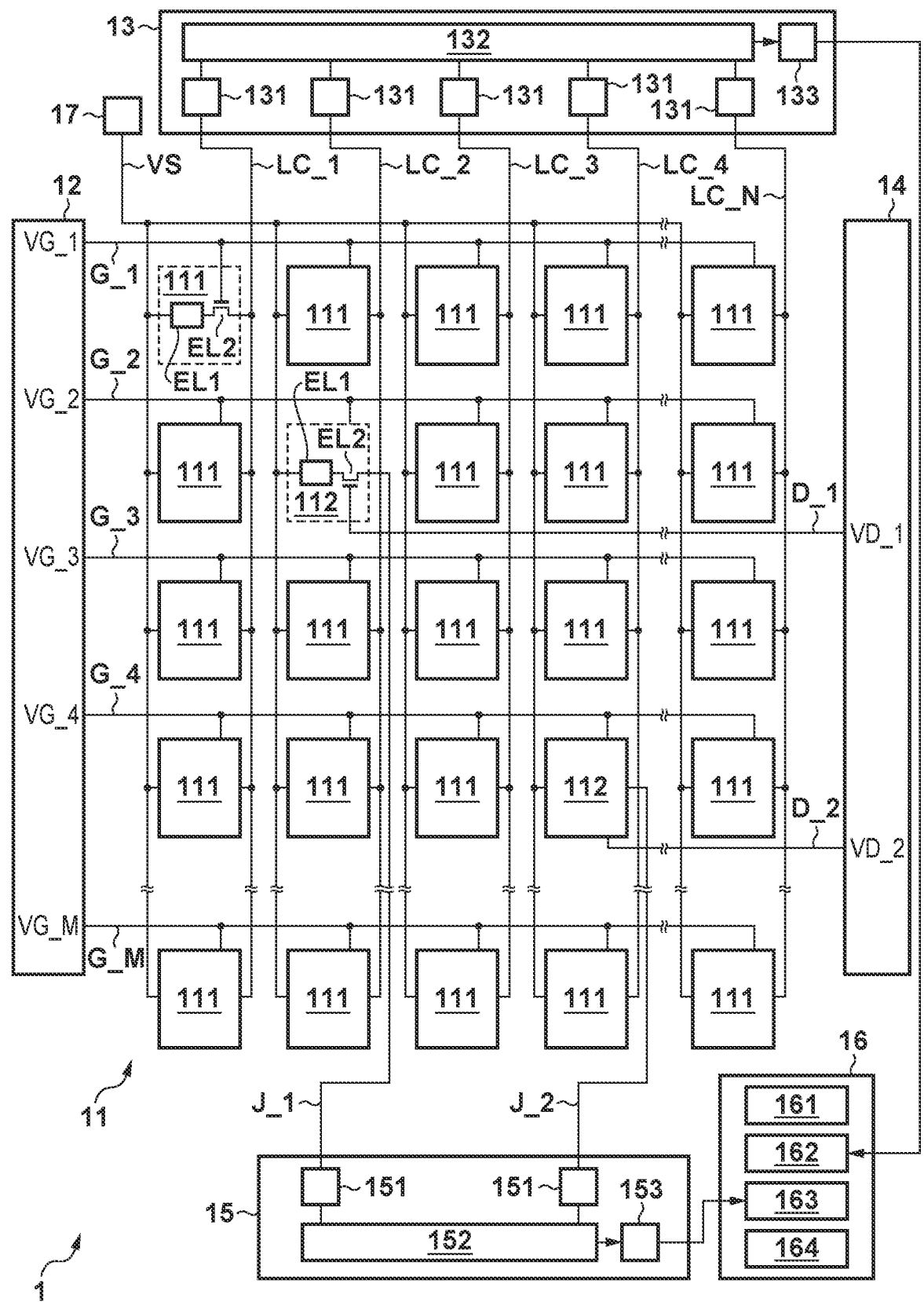
FIG. 2 is a block diagram for explaining an example of the arrangement of a radiation imaging apparatus.

FIG. 2 is a block diagram showing an example of the arrangement of the radiation imaging apparatus 1 according to this embodiment. The radiation imaging apparatus 1 includes a sensor array 11, an imaging driving unit 12, an imaging readout unit 13, an AEC driving unit 14, and an AEC readout unit 15, a control unit 16, and a voltage supply unit 17. Assume that the sensor array 11 has a so-called indirect conversion arrangement (an arrangement that converts radiation into light and converts the light into electrical signals) in this embodiment, and a scintillator (not shown) which converts radiation into light is arranged extending above the sensor array 11.

In this embodiment, two types of sensors, that is, imaging sensors 111 and AEC sensors 112 are arranged (so as to form a plurality of rows and a plurality of columns) in an array in the sensor array 11. In this embodiment, assume that the sensor array 11 is formed by M rows×N columns (M and N are integers).

The imaging sensors 111 are driven by the imaging driving unit 12 and occupy a large portion of the plurality of sensors forming the sensor array 11. The sensor signals of the sensors 111 are read out by the imaging readout unit 13. In addition, the AEC sensors 112 are driven by the AEC driving unit 14, and two or more sensors 112 are scattered and arranged in the sensor array 11 in this embodiment. The sensor signals from the sensors 112 are read out by the AEC readout unit 15. Note that although details will be described later, the sensors 112 are used to obtain radiation information (more specifically, the accumulated irradiation dose, the irradiation intensity, and the like) during irradiation, and the number of the sensors 112 may be 1.

In this case, as shown in FIG. 2, a control line G is arranged for each row (the control lines G corresponding to the first row, the second row, . . . the Mth row will be denoted as a control line G_1, a control line G_2, . . . , a control line G_M, respectively, for the sake of discrimination). A control signal VG (the control signals VG corresponding to the first row, the second row, . . . the Mth row will be denoted as a control signal VG_1, a control signal VG_2, . . . , a control signal VG_M, respectively, for the sake of discrimination) is transmitted from the imaging driving unit 12 for each control line G. In addition, a column signal line LC is arranged for each column (the column signal lines LC corresponding to the first column, the second column, . . . the Mth column will be denoted as a column signal line LC_1, a column signal line LC_2, . . . , a column signal line LC_M, respectively, for the sake of discrimination). Each column signal line LC is connected to the readout unit 13.

Each imaging sensor 111 includes a detection element EL1 and a switch element EL2 as exemplified by a sensor positioned at the first column of the first row in the sensor array 11. The detection element EL1 is, for example, a PIN sensor, and its one end is connected to a bias line VS and its other end is connected to the corresponding switch element EL2. The switch element EL2 is, for example, a thin-film transistor, and the gate terminal (control terminal) is connected to the corresponding control line G (the control line G_1 in the case of the sensor 111 at the first column of the first row). In addition, the source terminal is connected to the detection element EL1, and the drain terminal is connected to the corresponding column signal line LC (the column signal line LC_1 in the case of the sensor 111 at the first column of the first row).

The imaging driving unit 12 is a vertical scanning circuit formed by using, for example, a shift register or the like, and drives each corresponding sensor 111 by activating the control signals VG_1 to VG_M (by providing high-level signals in this embodiment). More specifically, the imaging driving unit 12 controls the conductive state or the non-conductive state of the switch element EL2 of each sensor 111 to accumulate charges or output a sensor signal corresponding to the charges in the detection element EL1 serving as the PIN sensor. The output sensor signal is read out by the imaging readout unit 13 via the corresponding column signal line LC.

The imaging readout unit 13 includes signal processing units 131, a multiplexer 132, and an output unit 133. Each signal processing unit 131 includes, for example, a signal amplification circuit and a sample-and-hold circuit. The multiplexer 132 is formed by using a plurality of switches, and transfers the sensor signal of each column sequentially to the output unit 133. The output unit 133 includes, for example, an analog-to-digital converter (AD converter), and the AD-converted sensor signal is output to the control unit 16 (to be described later) in this embodiment.

Note that the sensor signal may also indicate, other than the signal itself output from each sensor 111, a signal based on this output signal, that is, a signal that has undergone some kind of signal processing (for example, signal amplification, AD conversion, or the like) for the sake of descriptive convenience in this specification. For example, a sensor signal that has undergone AD conversion by the readout unit 13 after being output from a given sensor 111 will simply be referred to as a sensor signal. In a similar manner, this also applies to the sensor signal of each sensor signal 112 to be described next.

Although the AEC sensor 112 is arranged at a position on the second column of the second row and at a position on the fourth column of the fourth row of the sensor array 11 in FIG. 2, and the AEC sensors can be further arranged at other positions not shown in the drawing. Each sensor 112 has an arrangement similar to that of the sensor 111, but is connected to another control line different from the control line G and to another column line different from the column signal line LC. In the case of the sensor 112 at the position on the second column of the second row, the gate terminal of the switch element EL2 is connected to a control line D_1, and the source terminal is connected to a column signal line J_1. Also, in the case of the sensor 112 at the position on the fourth column of the fourth row, the gate terminal of the switch element EL2 is connected to a control line D_2, and the source terminal is connected to a column signal line J_2.

Each of the other sensors 112 (not shown) also has an arrangement similar to those described above. The gate terminal of the switch element EL2 is connected to a control line D_x (x=1, 2, . . . , K (K is an integer smaller than M)), and the source terminal is connected to a column signal line J_y (y=1, 2, . . . , L (L is an integer smaller than N)). The control line D_x transmits a control signal VD_x (x=1, 2, . . . , K) from the driving unit 14. In addition, the column signal J_y (y=1, 2, . . . , L) is connected to the readout unit 15.

The driving unit 14 is arranged in a manner similar to the driving unit 12 described above, that is, the driving unit is a vertical scanning circuit formed by using, for example, a shift register or the like, and drives each sensor 112 by activating the control signals VD_1 to VD_K. As a result, the sensor signal output from each sensor 112 is read out by the readout unit 15 via the corresponding column signal line J_y. The readout unit 15 is arranged in a manner similar to the imaging readout unit 13 described above, and includes signal processing units 151, a multiplexer 152, and an output unit 153. The signal processing units 151, the multiplexer 152, and the output unit 153 have functions similar to those of the signal processing units 131, the multiplexer 132, and the output unit 133, respectively.

The control unit 16 uses a reference signal such as a clock signal or the like to execute synchronization control of the above-described elements included in the radiation imaging apparatus 1, and controls the operation of each element required to implement radiation imaging by the apparatus 1. The control unit 16 also functions as an arithmetic operation unit that performs arithmetic processing to execute this control, arithmetic processing related to data obtained by this control, and the like. In this embodiment, the control unit 16 includes a timing generator 161, a data generator 162, an AEC determiner 163, and an interface 164.

The timing generator 161 generates a reference signal to perform synchronization control of the driving units 12 and 14 and the readout units 13 and 15. The data generator 162 generates image data based on the sensor signals of the sensors 111 received from the readout unit 13, and performs predetermined correction processing concomitantly on this image data. Although details will be described later, the determiner 163 generates an evaluation value to implement AEC suitably based on the sensor signals of the sensors 112 received from the readout unit 15, and determines whether the evaluation value satisfies a predetermined condition. The interface 164 is an interface for performing signal communication with an outside device, and receives, for example, parameters required for imaging from the computer 2 or transmits image data generated by the data generator 162 to the computer 2.

Although the control unit 16 is formed by an ASIC (application-specific integrated circuit) in this embodiment, the function of the control unit 16 may be implemented by another semiconductor IC such as a PLD (programmable logic device) or the like or may be implemented by a CPU and a memory. That is, the functions of the apparatus 1 described in this specification are implemented by the control performed by the control unit 16, and this control can be implemented either by hardware or software.

The voltage supply unit 17 supplies a power supply voltage corresponding to each element in the apparatus 1, and supplies a ground voltage to the sensors 111 and 112 in the sensor array 11 via the bias line VS in this embodiment.

The above-described arrangement of the radiation imaging apparatus 1 is merely an example, and the arrangement of the apparatus 1 is not limited to this. For example, although a mode in which a PIN sensor is used as the detection element EL1 has been exemplified in this embodiment, another photoelectric conversion element such as a MIS sensor or the like may be used as another embodiment. For example, although a mode in which the sensor array 11 has an indirect conversion arrangement has been exemplified in this embodiment, a so-called direct conversion arrangement (an arrangement in which radiation is directly converted into electrical signals) may be adopted as another embodiment. For example, although a mode in which the driving units 12 and 14 are arranged as separate units has been exemplified in this embodiment, these driving units may be formed by a single component. In a similar manner, the readout units 13 and 15 may also be formed by a single component. In addition, for example, the sensor 111 may be formed to also have the function of the sensor 112.

Figure 3:
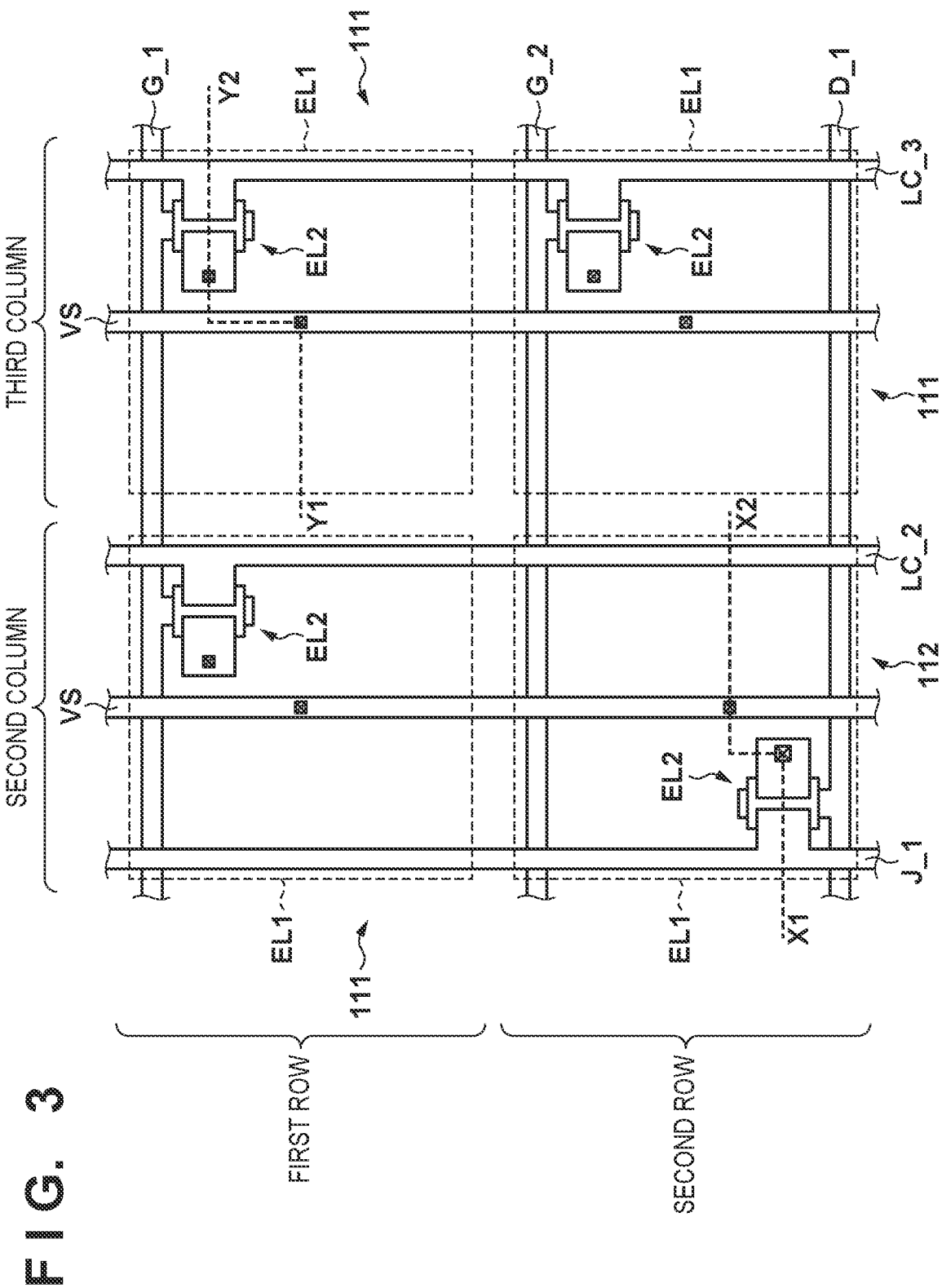
FIG. 3 is a diagram for explaining an example of the structure of the radiation imaging apparatus.
Figure 4A:
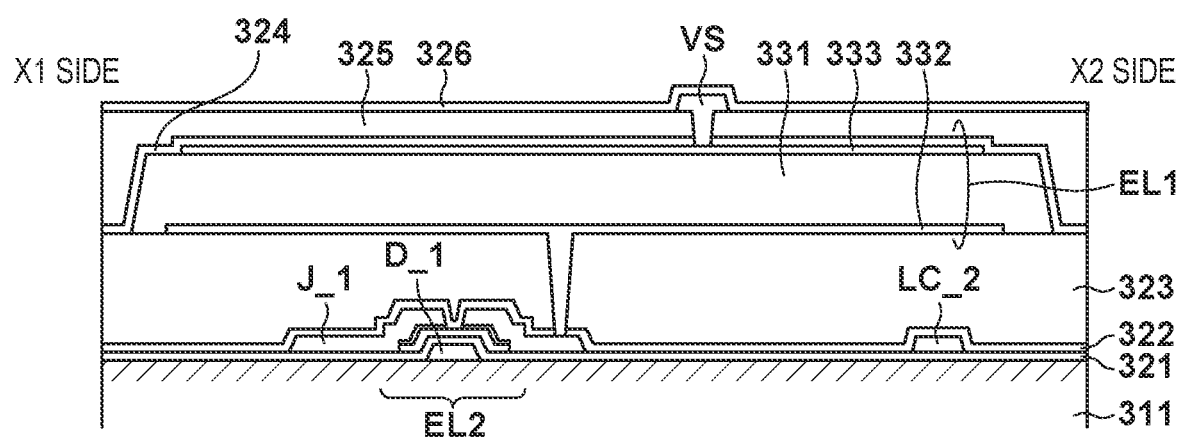
FIG. 4A is a view for explaining an example of the structure of the radiation imaging apparatus.
Figure 4B:
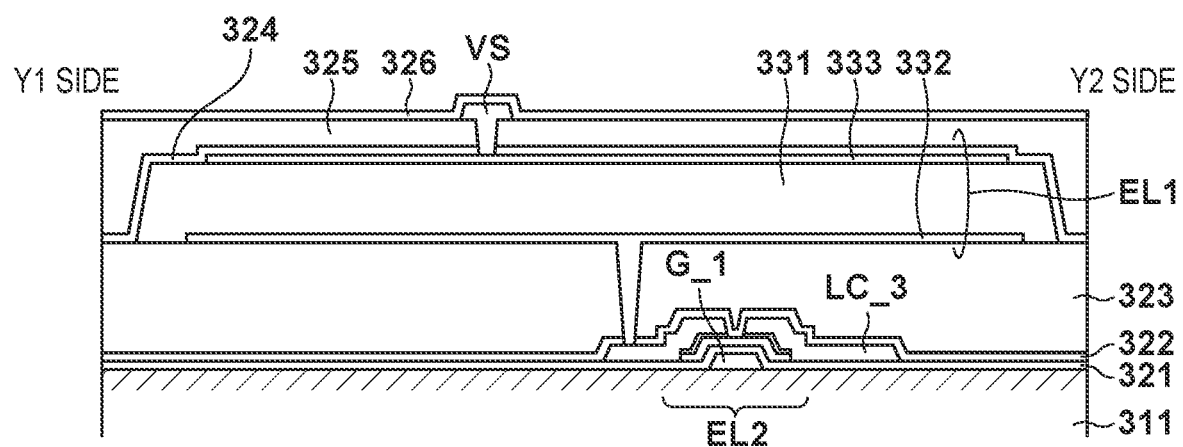
FIG. 4B is a view for explaining an example of the structure of the radiation imaging apparatus.

FIG. 3 shows an upper surface layout of a region at the first row to the second row and the second column to the third column of the sensor array 11. As described with reference to FIG. 2, the AEC sensor 112 is arranged at the position of the second column of the second row, and the imaging sensors 111 are arranged at positions other than this position. FIG. 4A shows a sectional structure taken along a line X1-X2 in FIG. 3, that is, a sectional structure of the sensor 112. FIG. 4B shows a sectional structure taken along a line Y1-Y2 in FIG. 3, that is, a sectional structure of the sensor 111. Each of the sensors 111 and 112 is formed by arranging a film, a member, and a layer (for example, a semiconductor member such as amorphous silicon or the like and an insulating film such as silicon oxide or the like) for forming the elements described above on an insulating substrate 311 made of glass or the like.

For example, paying attention to the sensor 112 (referring to FIGS. 3 and 4A), the control line D_1 formed integrally with the gate terminal of the switch element EL2, serving as a thin-film transistor, has been arranged on the substrate 311. Furthermore, an insulating film 321 is arranged so as to cover the above-described gate terminal (the control line D_1) on the substrate 311. A semiconductor member for forming a channel of the switch element EL2 is arranged on the above-described gate terminal via the insulating film 321, and electrodes for forming the drain terminal and the source terminal are arranged at both ends, respectively, of this semiconductor member.

The above-described drain terminal is formed integrally with the column signal line J_1, in other words, the column signal line J_1 extends to the switch element EL2 so as to form the above-described drain terminal. On the other hand, the above-described source terminal is connected to the detection element EL1 which is arranged above the source terminal via a protection film 322 and an interlayer insulating film 323. The detection element EL1 includes a semiconductor member 331 forming a p-n junction and a lower electrode 332 and an upper electrode 333 arranged on its lower surface side and its upper surface side, respectively, and the source terminal is in contact with the lower electrode 332 via a contact hole.

The bias line VS is arranged on the detection element EL1 via a protection film 324 and an interlayer insulating film 325, and the bias line VS is in contact with the upper electrode 333 via a contact hole. Furthermore, a protection 326 is arranged so as to cover the interlayer insulating film 325 and the bias line VS.

Note that although the sensor structure has been described above by paying attention to the sensor 112 (with reference to FIGS. 3 and 4A), the sensor structure of each sensor 111 (see FIGS. 3 and 4B) can be understood in a similar manner.

Figure 5:
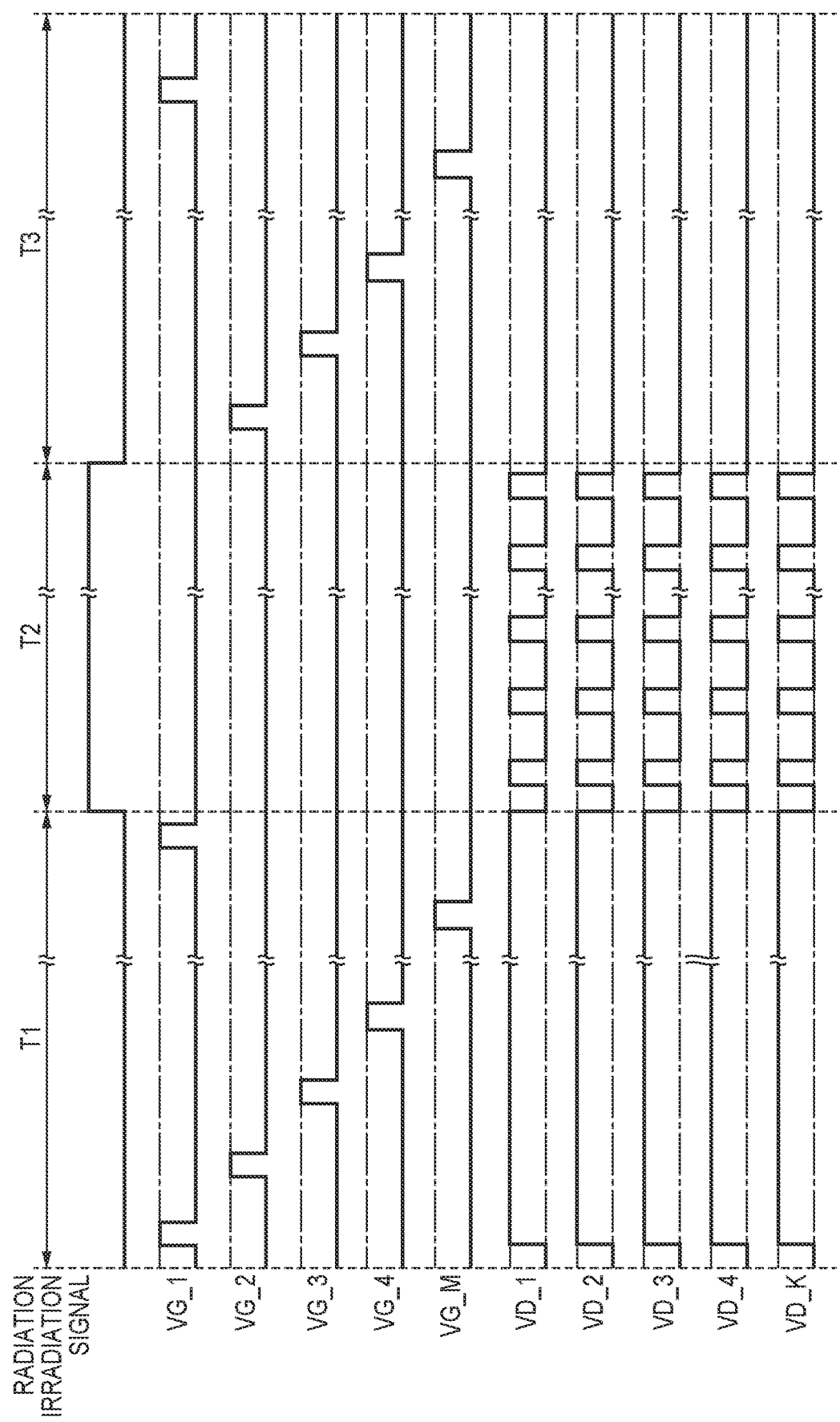
FIG. 5 is a timing chart for explaining an example of a driving method of the radiation imaging apparatus.

FIG. 5 is a timing chart for explaining an example of the driving method of the radiation imaging apparatus 1. In FIG. 5, the abscissa indicates a time axis, and the ordinate indicates signal levels of the radiation irradiation signal, the control signals VG_1 to VG_M, and the control signals VD_1 to VD_K. The radiation irradiation signal indicates the state of the control of the radiation source 6 by the radiation source control unit 5. For example, a case in which the radiation irradiation signal is at high level (H level) indicates that the radiation source 6 is in an active state, and a case in which the radiation irradiation signal is at low level (L level) indicates that the radiation source 6 is in an inactive state. That is, a state in which the radiation irradiation signal is at a high level indicates a state in which radiation irradiation is being performed.

In this embodiment, in a period T1 (for example, about several sec to several ten min) before the start of radiation irradiation, the start of radiation irradiation is detected based on the sensor signals from the AEC sensors 112 while noise components are removed from the imaging sensors 111. Next, in a period T2 (for example, about 1 [msec] to 1 [sec]) after the start of radiation irradiation has been detected, AEC is performed based on the sensor signals from the AEC sensor 112 while charge accumulation is performed in the imaging sensors 111. Details of the AEC according to this embodiment will be described later. A radiation irradiation end request is made based on this AEC (the radiation irradiation signal is set to L level), and a sensor signal corresponding to the accumulated charges described above is read out from each imaging sensor 111 in a subsequent period T3 (for example, about 10 [msec] to 100 [msec]). The details of the operation performed in each of the periods T1 to T3 will be described hereinafter.

First, in the period T1, H-level pulses (pulses maintained at H level over a predetermined period, for example, a period of about 1 [μsec] to 100 [μsec]) are sequentially output for the control signals VG_1 to VG_M. As a result, the imaging sensors 111 are driven sequentially for each row. More specifically, a noise component corresponding to a dark current is discharged from the detection element EL1 of each sensor 111 via the switch element EL2. During the period T1, the control unit 16 maintains the readout unit 13 in the inactive state to discard these discharged noise components. The series of H-level pulses of the control signals VG_1 to VG_M are repeatedly output (H-level pulses are output sequentially again starting from the control signal VG_1 after the H-level pulse has been output up to the control signal VG_M), thus initializing the sensor 111 of each row at a predetermined period.

On the other hand, during the period T1, the control signals VD_1 to VD_K are all maintained at H level, that is, the AEC sensors 112 are maintained in a driven state. During the period T1, the control unit 16 maintains the readout unit 15 in the active state, thus maintaining the readout of the sensor signals of the sensor 112 by the readout unit 15 as a result. Subsequently, the control unit 16 detects the start of radiation irradiation based on a change in the signal value of the sensor signal from each sensor 112. Assume that the start of radiation irradiation is detected at a timing after the H-level pulse of the control signal VG_1 has been output.

Next, in the period T2, the control signals VG_1 to VG_M are maintained at L level. As a result, charges corresponding to the radiation are accumulated in each imaging sensor 111. On the other hand, during the period T2, H-level pulses are output at a predetermined period for the control signals VD_1 to VD_K. As a result, the readout unit 15 reads out the sensor signal of each AEC sensor 112, and AEC (to be described later) is performed based on this signal.

In the period T3, after radiation irradiation has been ended appropriately by AEC described above, H-level pulses of the control signals VG_1 to VG_M are output, and the readout unit 13 reads out the sensor signals of the imaging sensors 111. In this case, in the period T1 described above, the radiation irradiation is started at the timing after the H-level pulse of the control signal VG_1 has been output, that is, a state in which the initialization of the sensors 111 of each row has been interrupted at a timing after the initialization has been performed for the first row but before the initialization is started for the second row is created. Hence, in the period T3, the output of the H-level pulse of the control signal VG_2 is started, and signal readout is performed sequentially from the sensors 111 of the second row. As a result, the charge accumulation time (that is, the period from the timing at which the final driving operation is performed in the period T1 until the timing at which the driving operation is started again at the period T3) of the sensors 111 of all of the first to Mth rows can be made equal to each other. Image data is generated based on sensor signals read out from the sensors 111 in this manner. On the other hand, during the period T3, each of the control signals VD_1 to VD_K is maintained at L level, and the control unit 16 may accordingly maintain the readout unit 15 in the inactive state.

Although an explanation was omitted in FIG. 5, correction data may be obtained after the sensor signals of the sensors 111 have been read out in the period T3. This correction data is image data obtained in a state without radiation irradiation and is also referred to as offset data. That is, after the period T3, a noise removal operation is performed for each sensor 111 by using a procedure similar to that in the period T1 under a state in which radiation irradiation is not performed. Subsequently, an operation to accumulate charges in each sensor 111 is performed over a period similar to the period T2, and an operation to read out a sensor signal from each sensor 111 is performed by using a procedure similar to that in the period T3. The correction data is obtained as a result. For example, after generating image data based on the sensor signals read out in the period T3, the data generator 162 of the control unit 16 can perform correction processing on the image data by using the correction data.

Figure 6:
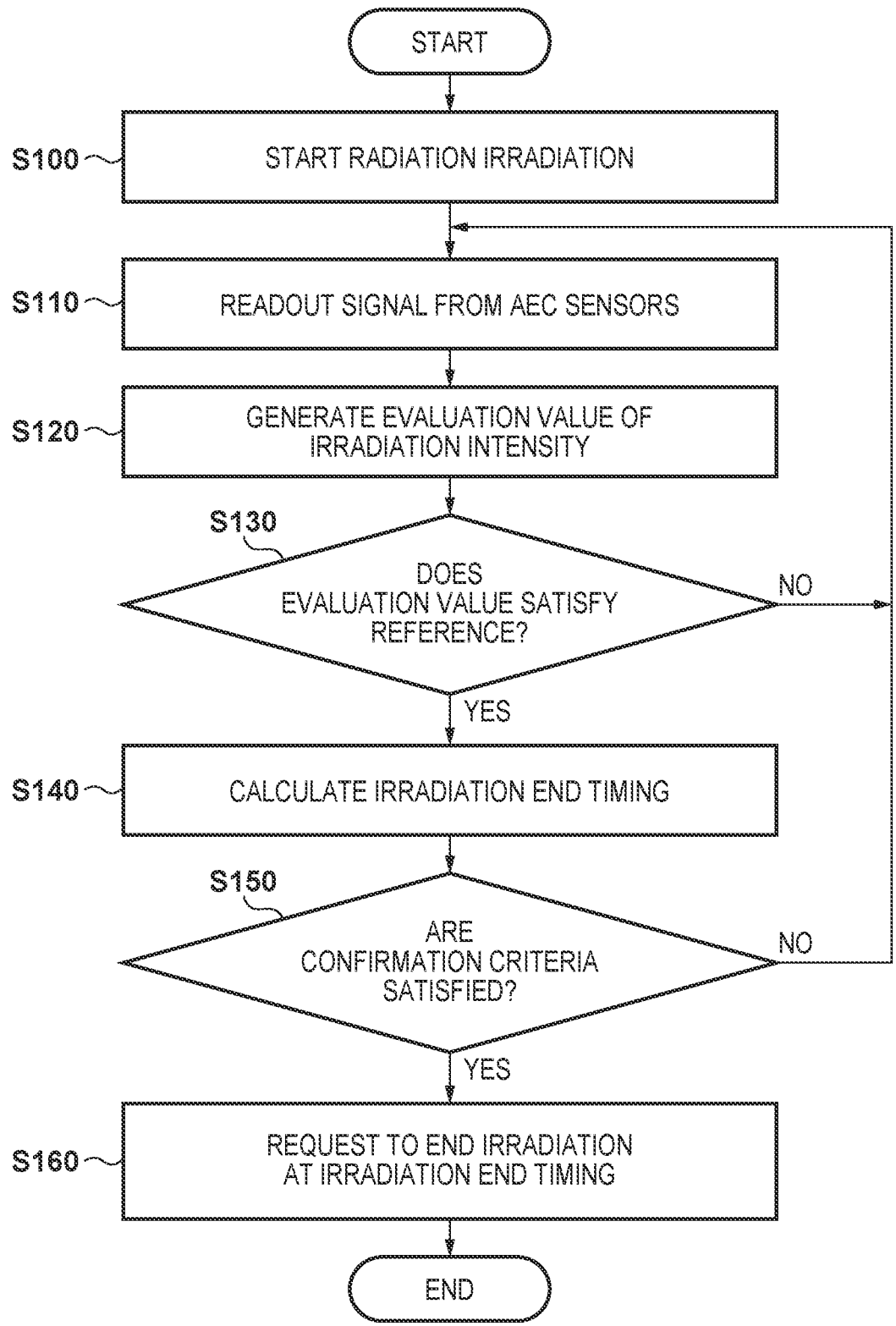
FIG. 6 is a flowchart for explaining an example of AEC.

FIG. 6 is a flowchart for explaining the method of AEC according to this embodiment. In this embodiment, the stability (degree of variation) of the radiation irradiation intensity (irradiation dose per unit time) is evaluated based on the sensor signal of each AEC sensor 112 read out periodically in the period T2.

As described above, the radiation irradiation time is determined based on the optimum value of the accumulated irradiation dose and the radiation irradiation intensity. Hence, to implement AEC appropriately (to make an irradiation end request without lack of radiation irradiation or excessive radiation irradiation), it is necessary to suitably predict the timing at which the accumulated irradiation dose reaches the optimum value. However, it is difficult to suitably predict this timing under a state in which the irradiation intensity has not stabilized. On the other hand, in general, although noise or the like can cause the irradiation intensity to be unstable immediately after the start of irradiation, the irradiation intensity tends to stabilize along with the elapse of time (the degree of variation of the irradiation intensity tends to decrease along with the elapse of time).

Therefore, in this embodiment, the stability of the irradiation intensity is evaluated at a predetermined period based on the sensor signal of each AEC sensor 112, and whether the irradiation end timing can be determined is determined based on this evaluation result. The contents of the flowchart to be described hereinafter are executed mainly by the control unit 16 (for example, the determiner 163) in the apparatus 1.

First, in step S100 (to be expressed simply as "S100" hereinafter, and this applies to other steps in a similar manner), radiation irradiation is started. Note that the detection of the start of radiation irradiation is performed in the manner of the operation (see FIG. 5) performed in the period T1.

In S110, sensor signals are read out from the AEC sensors 112. This is performed by outputting H-level pulses of the control signals VD_1 to VD_K in the manner of the operation (see FIG. 5) performed in the period T2.

In S120, the stability of the irradiation intensity is evaluated based on the sensor signals read out from the sensors 112 in S110, and an evaluation value indicating this stability is generated. This evaluation value indicates whether the degree of variation falls within the range of tolerance, and more specifically, indicates the degree of inconsistency (deviation amount) and/or the frequency of inconsistency between the irradiation intensity expected by the apparatus 1 and the actual irradiation intensity (detected value) detected by the apparatus 1 (the sensors 112). In this embodiment, the evaluation value is the rate of increase of the accumulated irradiation dose at the point of the evaluation (the time derivative of the accumulated irradiation dose). Alternatively/concomitantly, the signal value itself of each sensor signal read out in step S110 may be used as the evaluation value. Alternatively, the evaluation value may be generated based on at least one of an average value, a variance, and a standard deviation of the sensor signals of the sensors 112.

In S130, the control unit determines whether the evaluation value obtained in S120 satisfies a predetermine reference. This reference will be described later. If the evaluation value satisfies the reference, the process advances to S140. If the evaluation value does not satisfy the reference, the process returns to S110 (the evaluation and generation of the evaluation value described above are continued by reading out the sensor signals of the AEC sensors 112 until the evaluation value satisfies the reference).

In S140, the control unit calculates the irradiation end timing. This timing can be calculated based on, for example, the accumulated irradiation dose obtained up to that point and the irradiation intensity at that point.

In S150, the control unit determines whether the irradiation end timing calculated in S140 can be confirmed. This is performed by continuing the evaluation and generation of the evaluation value described above even after the evaluation value has satisfied the reference in S130. If the evaluation value has continued to satisfy the reference over a predetermined period, it is determined that the irradiation end timing can be confirmed. Since the readout of sensor signals of the sensor 112 is performed at a predetermined period in this embodiment, it will be determined that the irradiation end timing can be confirmed when an evaluation value based on a readout result of each period has, for example, successively satisfied the reference over two or more times. If the irradiation end timing can be confirmed, the process advances to S160. If the irradiation end timing cannot be confirmed, the process returns to S110 (the irradiation end timing will be updated or recalculated by performing the processes of S130 and S140 in this case).

Note that as another embodiment, the process of S150 can be omitted (the determination contents of S150 may be substantially included in the process of S130) by setting an evaluation value that takes the elapse of time into consideration by using, for example, the average value, the variance, the standard deviation, or the like of the sensor signals of the sensors 112.

In S160, the control unit makes a radiation irradiation end request at the timing calculated in S140 and confirmed in S150. This can be performed by outputting a signal indicating the irradiation end request from the control unit 16 of the apparatus 1 to the radiation source control unit 5 via the computer 2. As a result, the operation of the period T2 ends, and the processing shifts to the operations of the period T3 and subsequent periods (see FIG. 5).

Although this embodiment assumed that the control unit 16 of the apparatus 1 will mainly perform the processes of steps S100 to S160, the processes of some of the steps may be performed by the computer 2 or by the radiation source control unit 5 as another embodiment. This can reduce, for example, the delay in the control of the radiation source 6. For example, the computer 2 may perform some or all of the operations for the evaluation in S120, the determination in S130, the calculation in S140, the determination in S150, and the irradiation end request in S160. In such a case, the arrangement of the radiation imaging system SY may be changed so that the computer 2 will implement some or all of the functions of the control unit 16, for example, the determiner 163.

A case in which the processes of steps until S150 will be performed by the apparatus 1 and only the process of S160 will be performed by the computer 2 will be considered as an example. In this case, in response to the stabilization of the irradiation intensity, the control unit 16 of the apparatus 1 will calculate the irradiation end timing based on the accumulated irradiation dose up to that point and the stabilized irradiation intensity. Subsequently, the computer 2 will receive the calculation result from the control unit 16 and make an irradiation end request to the radiation source control unit 5 at the timing indicated in the calculation result.

A case in which the processes until S130 will be performed by the apparatus 1 and the processes of S140 and its subsequent steps will be performed by the computer 2 will be considered as another example. In this case, the control unit 16 of the apparatus 1 functions as a signal generation unit that generates and outputs a signal indicating the stabilization of the irradiation intensity or functions as a notification unit that notifies a signal output destination (the computer 2 in this case) of the stabilization of the irradiation intensity. Subsequently, in response to this, the computer 2 calculates the irradiation end timing based on the accumulated irradiation dose up to that point and the stabilized irradiation intensity, and makes an irradiation end request to the radiation source control unit 5 at the calculated timing.

A case in which the processes until S110 will be performed by the apparatus 1 and the processes of S120 and its subsequent steps will be performed by the computer 2 will be considered as yet another example. In this case, the apparatus 1 need only be formed to be able to output the sensor signals of the AEC sensors 112 to the computer 2, that is, the control unit 16 need only function in a conventional manner. The computer 2 need only be arranged to be able to communicate with the apparatus 1, and will implement AEC by receiving the sensor signals of the AEC sensors 112 from the apparatus 1 and performing the processes of step S120 and its subsequent steps based on these sensor signals.

Alternatively, the processes until S110 may be performed by the apparatus 1, the processes of S120 to S150 may be performed by the computer 2, and only the process of S160 may be performed by the radiation source control unit 5. In this case, the computer 2 will operate as an AEC control apparatus during the period of period T2 (see FIG. 5). That is, based on the sensor signals of the sensors 112 received from the apparatus 1, the computer 2 will function as a signal generation unit that generates and outputs a signal indicating the stabilization of the irradiation intensity or a notification unit that notifies the radiation source control unit 5 of the stabilization of the irradiation intensity.

In summary, in this embodiment, after the start of radiation irradiation, the sensor signals of the AEC sensors 112 are read out at a predetermined period (S110), the degree of stability of the irradiation intensity is evaluated based on the sensor signals, and an evaluation value indicating this degree of stability is generated (S120). Subsequently, if this evaluation value satisfies a reference (S130), it will be determined that the irradiation end timing can be calculated (S140). Subsequently, the evaluation described above is continued, and whether the calculation result of the irradiation end timing can be confirmed is determined based on the new evaluation value obtained by the continued evaluation operation (S150). Note that the calculation result of the irradiation end timing can be updated based on the new evaluation value as described above (S140). Subsequently, a radiation irradiation end request is made at the calculated and confirmed timing, and the AEC ends (S160). This series of operations may be partially performed by an apparatus (for example, the computer 2) outside the radiation imaging apparatus 1.

More specific examples, that is, modifications of the AEC according to this embodiment will be described with reference to FIGS. 7A to 7C hereinafter.

First Example

FIG. 7A is a timing chart for explaining the first example of the AEC according to this embodiment. The abscissa of FIG. 7A indicates a time axis. In addition, the ordinate indicates the radiation irradiation signal (similar to that in FIG. 5), the accumulated irradiation dose of radiation, the evaluation value of irradiation intensity, the timings of various kinds of operations (signal readout of the AEC sensors 112 (S110 of FIG. 6), the output of the evaluation value (S120), and the determination (S130)), and the results of the various kinds of determinations (the determination in S130 and the determination in S150).

In this example, assume that, ideally, the accumulated irradiation dose will increase linearly (will increase in a manner indicated by broken lines in FIG. 7A) and that, ideally, the irradiation intensity will be constant. In addition, assume that the readout of sensor signals of the AEC sensors 112 (S110), the above-described evaluation and the generation of an evaluation value (S120), and the determination based on the evaluation value (S130) are performed in the same period.

According to FIG. 7A, the accumulated irradiation dose does not increase linearly immediately after the start of radiation irradiation (will increase while indicating an amplitude fluctuation due to noise), and will increase linearly in accordance with the elapse of time. Hence, it is difficult to predict a suitable radiation irradiation end timing at, for example, a timing in which the time has not sufficiently elapsed from the start of radiation irradiation such as the timing immediately after the start of radiation irradiation, and it may be difficult to implement AEC appropriately.

For example, the accumulated irradiation dose indicated by reference symbol P1 in FIG. 7A is higher than the expected accumulated irradiation dose (the ideal value indicated by broken lines). Hence, if the irradiation end timing is determined based on the timing of P1, the irradiation end timing will be determined based on a prediction that the accumulated irradiation dose will increase in a manner indicated by alternate long and dashed lines. In this case, the irradiation end request will be made at a timing which is much earlier than the ideal timing, and a state where there is insufficient radiation irradiation may occur as a result.

On the other hand, for example, the accumulated irradiation dose indicated by reference symbol P2 in FIG. 7A is lower than the expected accumulated irradiation dose described above. Hence, if the irradiation end timing is determined based on the timing of P2, the irradiation end timing will be determined based on a prediction that the accumulated irradiation dose will increase in a manner indicated by alternate long and two dashed lines. In this case, the irradiation end request will be made at a timing much later than the ideal timing, and a state where there is excessive radiation irradiation may occur as a result.

Hence, in this example, the timing at which the suitable irradiation end timing can be predicted is determined based on the stability of the irradiation intensity, and the irradiation end timing is calculated after this prediction can be made. This is because a future accumulated irradiation dose can be predicted adequately when the irradiation intensity has stabilized, and this allows the timing at which the accumulated irradiation dose reaches the optimum value, that is, the suitable irradiation end timing to be calculated as a result. As described above, the stability of the irradiation intensity is evaluated based on the sensor signals of the sensors 112, and an evaluation value indicating this stability is generated (see S110 and S120 of FIG. 6).

As described above, the evaluation and the generation of the evaluation value described above are performed periodically in this example. FIG. 7A shows a plot of an evaluation generated for each period and the determination result (S130 of FIG. 6) for each evaluation value. "○" is indicated as the determination result when the evaluation value falls within the reference range, and "x" is indicated as the determination result when the evaluation value does not fall within the reference range. Below the determination result of each evaluation value, the result of determination (S150 of FIG. 6) performed to confirm the irradiation end timing for each period is shown. "○" is indicated as the result of this determination when the evaluation value falls within the reference range consecutively (two consecutive periods) and "x" is indicated as the result of this determination when the evaluation value does not fall within the reference range consecutively. That is, it will be determined that the irradiation intensity has stabilized to a tolerable level (to a level that allows a suitable irradiation end timing to be calculated) when the evaluation value generated in each period falls within the reference range consecutively. Note that the number of times that the evaluation value should fall within the reference range consecutively for this determination may be a fixed value, may be set based on the irradiation intensity, or may be set based on the fluctuation amount of the evaluation value generated for each period.

In this example, neither the evaluation value corresponding to the timing of P1 nor the evaluation value corresponding to the timing of P2 falls within the reference range. On the other hand, at a further later timing of P3, the evaluation value has fallen within the reference range for two consecutive periods, and a state in which the irradiation timing can be confirmed has been set. Hence, in this example, the irradiation end timing is confirmed at the timing of P3. In this example, assume that the readout of the sensor signals of the AEC sensors 112, the evaluation and generation of the evaluation value as described above, and the determination based on the evaluation value will end or stop after the confirmation (after the timing of P3). Subsequently, an optimum radiation irradiation operation in which the accumulated irradiation dose is at an optimum amount is implemented by making an irradiation end request at the above-described irradiation end timing.

Although this example showed a mode in which the readout of the sensor signals of the AEC sensors 112, the evaluation and generation of the evaluation value as described above, and the determination based on the evaluation value are performed in the same period, these operations may be performed in periods different from each other. For example, the generation of the evaluation value may be performed once after the readout of the sensor signals of the AEC sensors 112 has been performed twice or more. Also, the determination based on the evaluation value may be performed once after the generation of the evaluation value has been performed twice or more. Alternatively, the period of each operation described above may change in accordance with the elapse of time (the execution interval of each operation may be changed in accordance with the elapse of time).

In addition, although this example showed a mode in which the accumulated irradiation dose increases linearly in an ideal state, that is, a mode which assumes that the ideal value of the irradiation intensity is constant, the ideal value of the irradiation intensity need not always be constant and may, for example, change in accordance with the elapse of time based on a predetermined function. In such a case, the reference range of the evaluation value will be set to change in accordance with the elapse of time. That is, it is sufficient for the condition (the reference range in this example) to be satisfied by the evaluation value to be set based on the expected accumulated irradiation dose or the irradiation intensity, and the condition may be set based on, for example, the imaging information input in advance by the user by using the input terminal 3. In addition, in this case, the evaluation value can be generated based on an element other than the rate of increase of the accumulated irradiation dose (the gradient of the accumulated irradiation dose in FIG. 7A). For example, the evaluation value may be generated by using an average value, a variance, and a standard deviation of the sensor signals of the sensors 112 obtained up to that point or may be generated by a weighted addition of several signals (the weighted addition coefficient may change in accordance with the elapse of time).

Second Example

FIG. 7B shows a timing chart for explaining a second example of AEC according to this embodiment in a manner similar to the first example (see FIG. 7A) described above. This example differs from the above-described first example mainly in the point that the readout of the sensor signals of the AEC sensors 112 (S110 of FIG. 6), the evaluation and the generation of the evaluation value as described above (S120), and the determination based on the evaluation value (S130) are continued even after the radiation irradiation end timing has been confirmed. According to this example, the irradiation end timing can be updated based on the evaluation result and/or the sensor signals of the sensors 112 which are obtained after the timing of P3, thus allowing the accuracy of AEC to be improved.

In this case, it is possible to consider a state in which the evaluation value exceeds the reference range at, for example, a timing indicated by P4 in FIG. 7B due to some kind of noise mixing into the radiation imaging apparatus 1 or the radiation source 6. However, in a case in which an evaluation result which does not satisfy the reference is generated after changing to a state in which the irradiation end timing can be confirmed, that is, after the timing of P3, the updating of the irradiation end timing is omitted, and such an evaluation result and the sensor signals of the sensors 112 which are used as the basis of this evaluation result will not be employed. This will allow the accuracy of AEC to be maintained.

Note that the number of times the above-described irradiation end timing is to be updated may be set to, for example, a predetermined number or may be set by the user by using the input terminal 3. Alternatively, the number of updates may be set based on the stabilized irradiation intensity or may be set based on another evaluation result (for example, the standard deviation) based on the sensor signals of the sensors 112.

Third Example

Figure 7C:
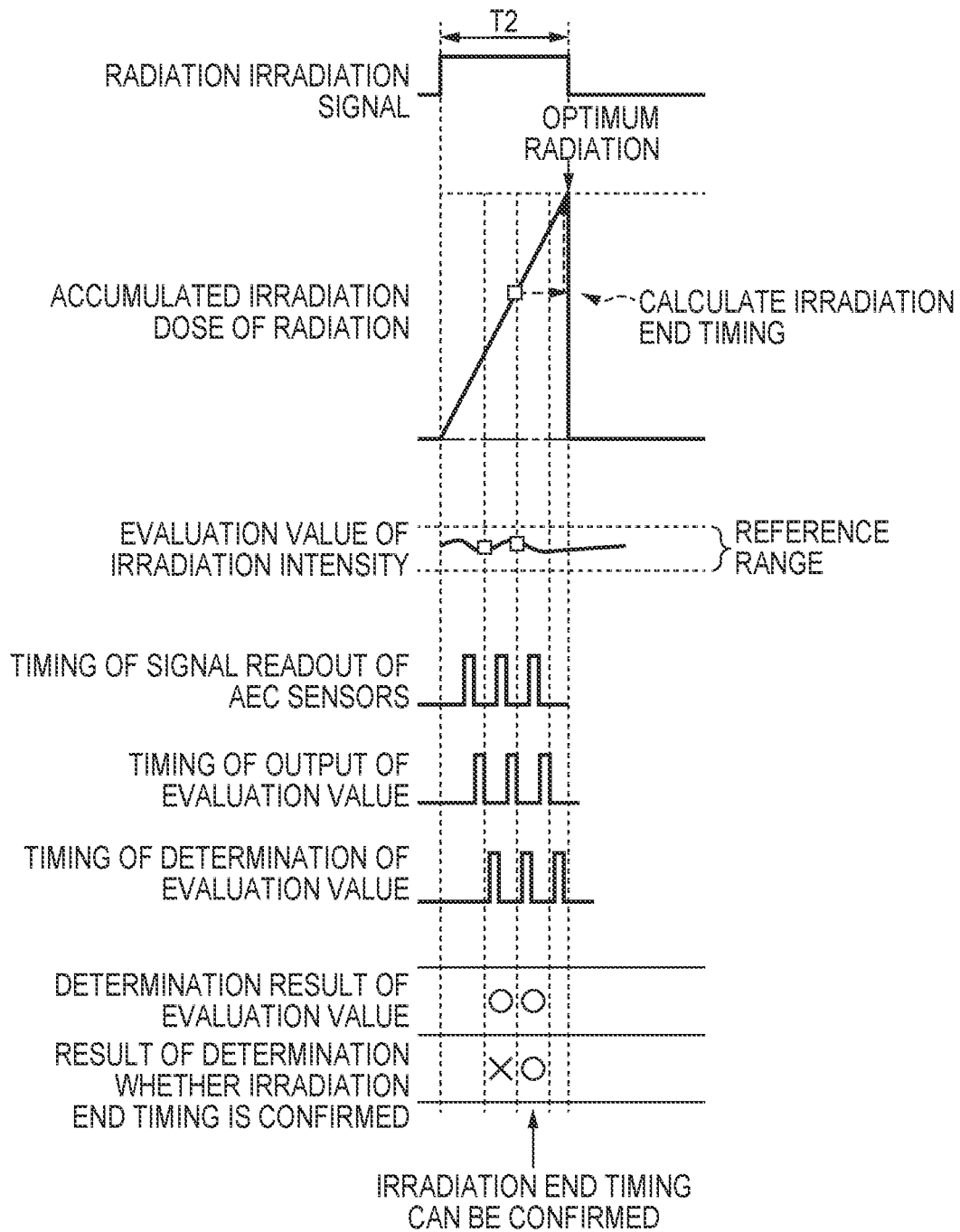
FIG. 7C is a timing chart for explaining yet another more specific example or yet another modification of the AEC.

FIG. 7C is a timing chart for explaining the third example of AEC according to this embodiment in a manner similar to the first example (see FIG. 7A) described above. This example shows a mode of a case in which the radiation irradiation intensity is comparatively high. In a case in which the irradiation intensity is comparatively high, it tends to be difficult for noise to mix into the radiation imaging apparatus 1 or the radiation source 6 or a signal component corresponding to the noise tends to be buried in the sensor signals of the sensors 112. Hence, as is obvious from FIG. 7C, the evaluation value generated based on the above-described evaluation (S120 of FIG. 6) will fall within the reference range consecutively even immediately after the start of irradiation, and a state in which the irradiation end timing can be confirmed can be created (S150). In other words, AEC according to this embodiment is effective for particularly cases in which the irradiation intensity is comparatively low.

Second Embodiment

Figure 8:
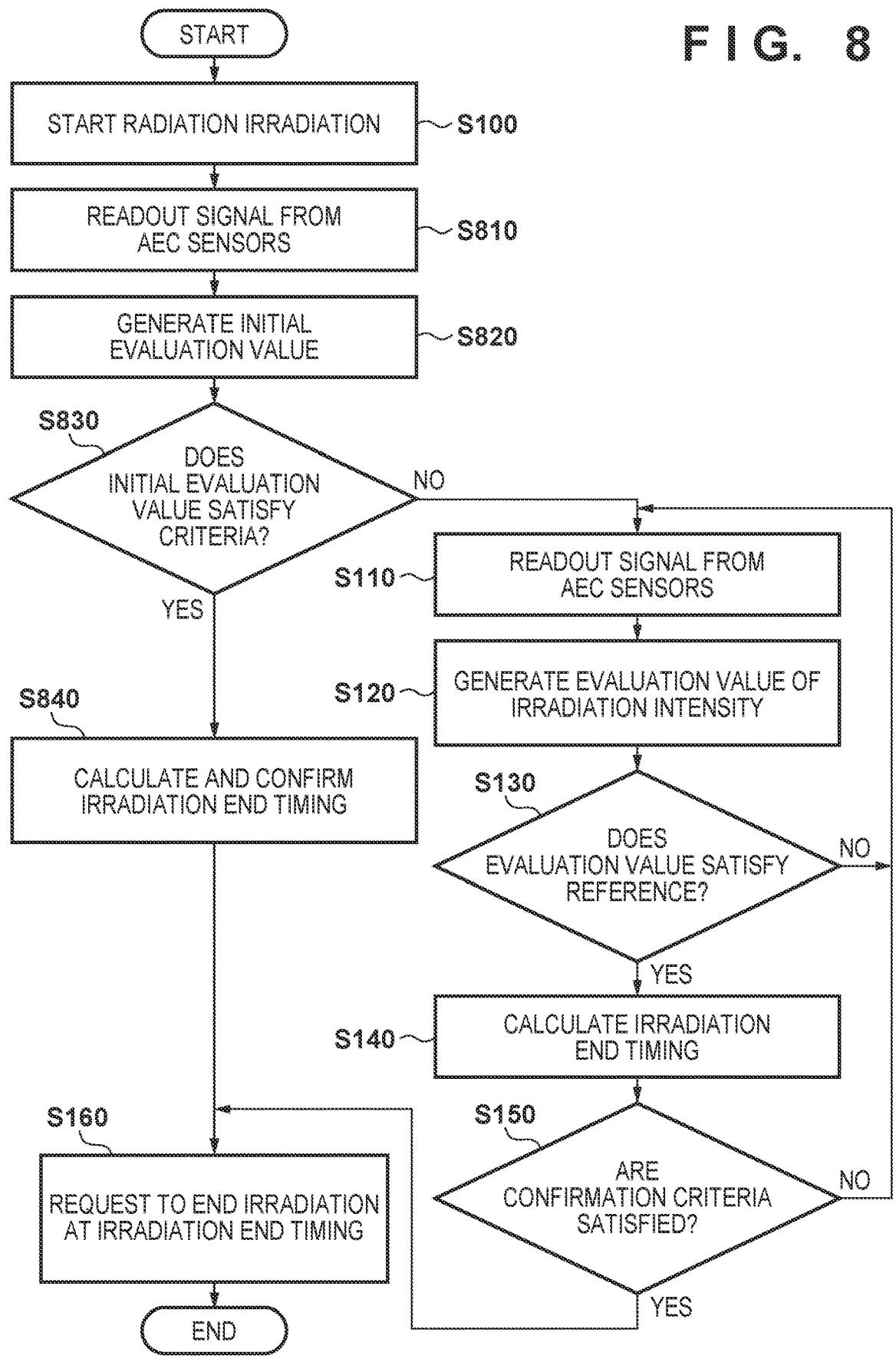
FIG. 8 is a flowchart of explaining another example of AEC.

A flowchart for explaining a method of AEC according the second embodiment will be described with reference to FIG. 8 in a manner similar to FIG. 6 (see the first embodiment). As described above, in a case in which the radiation irradiation intensity is comparatively high, it tends to be difficult for noise to mix into a radiation imaging apparatus 1 or a radiation source 6 or a signal component corresponding to the noise tends to be buried in the sensor signals of AEC sensors 112. Hence, the irradiation end timing can be quickly confirmed in a case in which the irradiation intensity is comparatively high.

In this embodiment, after the start of the radiation irradiation, an initial determination as to whether the irradiation intensity is comparatively high will be performed first. If the irradiation intensity is comparatively high, the irradiation end timing will be calculated and confirmed by using the result of this initial determination. On the other hand, if the irradiation intensity is comparatively low, AEC will be performed by using a procedure (S110 to S150 of FIG. 6) similar to that of the first embodiment. Details will be described hereinafter with reference to FIG. 8.

After radiation irradiation is started in S100, a sensor signal is read out from each AEC sensor 112 in S810. Next, in S820, an initial evaluation value is generated by performing an initial evaluation as to whether the irradiation intensity exceeds a reference value based on the sensor signal of each sensor 112. This initial evaluation value may be the signal value of the sensor signal of each sensor 112 or may be obtained by multiplying the signal value by a predetermined coefficient.

In S830, a determination as to whether the above-described initial determination, more specifically, the initial evaluation value obtained in S820 satisfies a reference is performed. In this embodiment, in a case in which the initial evaluation value is larger than the reference value, that is, in a case in which the irradiation intensity is comparatively high, the process will advance to S840. In a case in which the initial evaluation value is smaller than the reference value, that is, in a case in which the irradiation intensity is comparatively low, the process advances to S110 (in a similar manner to FIG. 6). For example, in a case in which the optimum value of the accumulated irradiation dose is 1 [mR], this reference value can be to a value (that is, 0.5 [mR]) corresponding to half of this optimum value (note that 1 [R]≈2.58×10$^{-4}$ [C/Kg]).

In S840, the irradiation end timing is calculated and confirmed. The irradiation end timing is calculated based on the initial evaluation value (substantially, the sensor signals read out in S810). As described above, it is difficult for the above-described mixing of noise to occur or the signal component corresponding to the above-described noise tends to be buried in sensor signals of the sensors 112 when the irradiation intensity is comparatively high. Hence, it is determined that the timing calculated here need not be updated (see the first embodiment), and the timing is immediately confirmed in this embodiment. Subsequently, in S160, a radiation irradiation end request is transmitted at the calculated and confirmed timing.

According to this embodiment, an initial determination as to whether the irradiation intensity is comparatively high is performed, and the initial determination result is used to quickly confirm the irradiation end timing when the irradiation intensity is comparatively high. As a result, the steps of S110 to S150 can be omitted, and it is possible to prevent, for example, the occurrence of a state in which the accumulated irradiation dose will exceed the optimum value before the irradiation end timing is confirmed.

According to the present invention, an irradiation end timing can be determined suitably.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus that includes a sensor configured to detect radiation and a control unit, wherein
  the control unit generates, after the start of radiation irradiation, an evaluation value indicating the stability of a radiation irradiation intensity based on a sensor signal from the sensor, and
  the control unit outputs, in response to the evaluation value satisfying a predetermined condition, a signal indicating that the radiation irradiation intensity has stabilized.

2. The radiation imaging apparatus according to claim 1, wherein the evaluation value is based on at least one of the signal value, an average value, a variance, a standard deviation of the sensor signal.

3. The radiation imaging apparatus according to claim 1, wherein the control unit notifies an output destination of the signal that a radiation irradiation end timing can be confirmed.

4. The radiation imaging apparatus according to claim 1, wherein the control unit generates the evaluation value periodically and outputs the signal when the generated evaluation value has satisfied a reference consecutively.

5. The radiation imaging apparatus according to claim 4, further comprising:
  an arithmetic operation unit configured to calculate, in response to receiving the signal, the radiation irradiation end timing.

6. The radiation imaging apparatus according to claim 4, wherein the control unit ends the generation of the evaluation value after the signal has been output.

7. The radiation imaging apparatus according to claim 4, further comprising:
an arithmetic operation unit configured to calculate, in response to receiving the signal, the radiation irradiation end timing,
wherein the control unit continues the generation of the evaluation value even after the signal has been output, and the arithmetic operation unit updates the radiation irradiation end timing that has been calculated.

8. The radiation imaging apparatus according to claim 1, wherein the control unit omits the generation of the evaluation value in a case in which the sensor signal from the sensor is larger than a reference value, and generates the evaluation value in a case in which the sensor signal is smaller than the reference value.

9. A radiation imaging system comprising:
a radiation imaging apparatus defined in claim 1; and
a radiation source.

10. A control apparatus that is formed to be capable of communicating with a radiation imaging apparatus which includes a sensor configured to detect radiation, the apparatus comprising:
a signal generation unit configured to evaluate, after the start of radiation irradiation to the radiation imaging apparatus, the stability of a radiation irradiation intensity based on a sensor signal from the sensor, and generate, in response to an evaluation value indicating the stability has satisfied a predetermined condition, a signal indicating that the radiation irradiation intensity has stabilized.

11. A control method of a radiation imaging apparatus which includes a sensor configured to detect radiation, the method comprising:
a step of generating, after the start of radiation irradiation, an evaluation value indicating the stability of a radiation irradiation intensity based on a sensor signal from the sensor; and
a step of outputting, in response to the evaluation value satisfying a predetermined condition, a signal indicating that the radiation irradiation intensity has stabilized.

* * * * *